United States Patent [19]
Ibea et al.

[11] Patent Number: 5,861,379
[45] Date of Patent: Jan. 19, 1999

[54] CHIMERIC FATTY BODY-PRO-GRF ANALOGS WITH INCREASED BIOLOGICAL POTENCY

[75] Inventors: Michel Ibea; Thierry Abribat; Paul Brazeau, all of Montréal, Canada

[73] Assignee: Theratechnologies Inc., Montreal, Canada

[21] Appl. No.: 702,114

[22] Filed: Aug. 23, 1996

Related U.S. Application Data

[63] Continuation-in-part of Ser. No. 651,645, May 22, 1996, abandoned, and Ser. No. 453,067, May 26, 1995, abandoned.

[51] Int. Cl.⁶ .......................... A61K 38/25; C07K 14/60
[52] U.S. Cl. .......................... 514/12; 530/324; 530/345; 530/399; 530/402; 930/120
[58] Field of Search .................... 530/324, 345, 530/399, 402; 514/12; 930/120

[56] References Cited

U.S. PATENT DOCUMENTS

| | | | |
|---|---|---|---|
| 4,622,312 | 11/1986 | Felix et al. | 514/12 |
| 4,870,054 | 9/1989 | Recker | 514/12 |
| 5,061,690 | 10/1991 | Kann et al. | 514/12 |
| 5,065,748 | 11/1991 | Bercu | 128/630 |
| 5,597,797 | 1/1997 | Clark | 514/12 |

OTHER PUBLICATIONS

Gaudreau et al., "Affinity of Human Growth Hormone-Releasing Factor (1–29)NH2 Analogues for GRF Binding Sites in Rat Adenopituitary", J. Med. Chem., vol. 35, pp. 1864–1869, 1992.

Coy et al., "Differential Effects of N–Terminal Modification on the Biological Potencies of Growth Hormone Releaseing Factor Analogues with Varying Chain Lengths", J. Med. Chem., vol. 30, pp. 219–222, 1987.

Muranishi et al, Pharmaceutical Research, vol. 8, No. 5, pp. 649–652 (1991).

Gross et al, The Peptides, vol. 3, Academic Press, pp. 1–341 (1981).

Merrifield, J. Am. Chem. Soc., 85:2149–2154 (1963).

Merrifield, J. Am. Chem. Soc., 86:304–305 (1964).

Castro et al, Tetrahedron Letters, No. 14, pp. 1219–1222 (1975).

Mergler et al, Peptides, Chemistry and Biology, Proc. of the 10th American Peptide Symp., St. Louis, pp. 259–260 (1987).

Dubreuil et al, J. Anim. Sci., vol. 68, pp. 1254–1268 (1990).

Abribat et al, Clinical Endocrinology, vol. 39, pp. 583–589 (1993).

Gaudreau et al, J. Med. Chem., vol. 35, pp. 1864–1869 (1992).

Coy et al, J. Med. Chem., vol. 30, pp. 219–222 (1987).

Gaudreau, Pierrette et al. Affinity of Human Growth Hormone–Releasing Factor (1–29)NH2 Analogues for GRF binding Sites in Rat Adenopituitary. J. Med. Chem. 1992, 35(10), 1864–1869, May 15, 1992.

Coy, D.H. et al. Differential effecst of N–terminal modifications on the biolgical potencies of growth hormone releasing factor analogues with varying chain lengths. J. Med. Chem. Oct. 1987, 30, 219–222.

*Primary Examiner*—Cecilia J. Tsang
*Assistant Examiner*—Anish Gupta
*Attorney, Agent, or Firm*—Evenson, McKeown, Edwards & Lenahan, P.L.L.C.

[57] ABSTRACT

The present invention relates to chimeric fatty body-pro-GRF analogs with increased biological potency, their application as anabolic agents and in the diagnosis and treatment of growth hormone deficiencies. The chimeric fatty body-pro-GRF analogs include an hydrophobic moiety (tail), and can be prepared, either by anchoring one or several hydrophobic tails to the GRF, or by substituting one or several amino-acids by a pseudomicellar residue in the chemical synthesis of GRF. The GRF analogs of the present invention are biodegradable, non-immunogenic and exhibit an improved anabolic potency with a reduced dosage and prolonged activity.

17 Claims, 5 Drawing Sheets

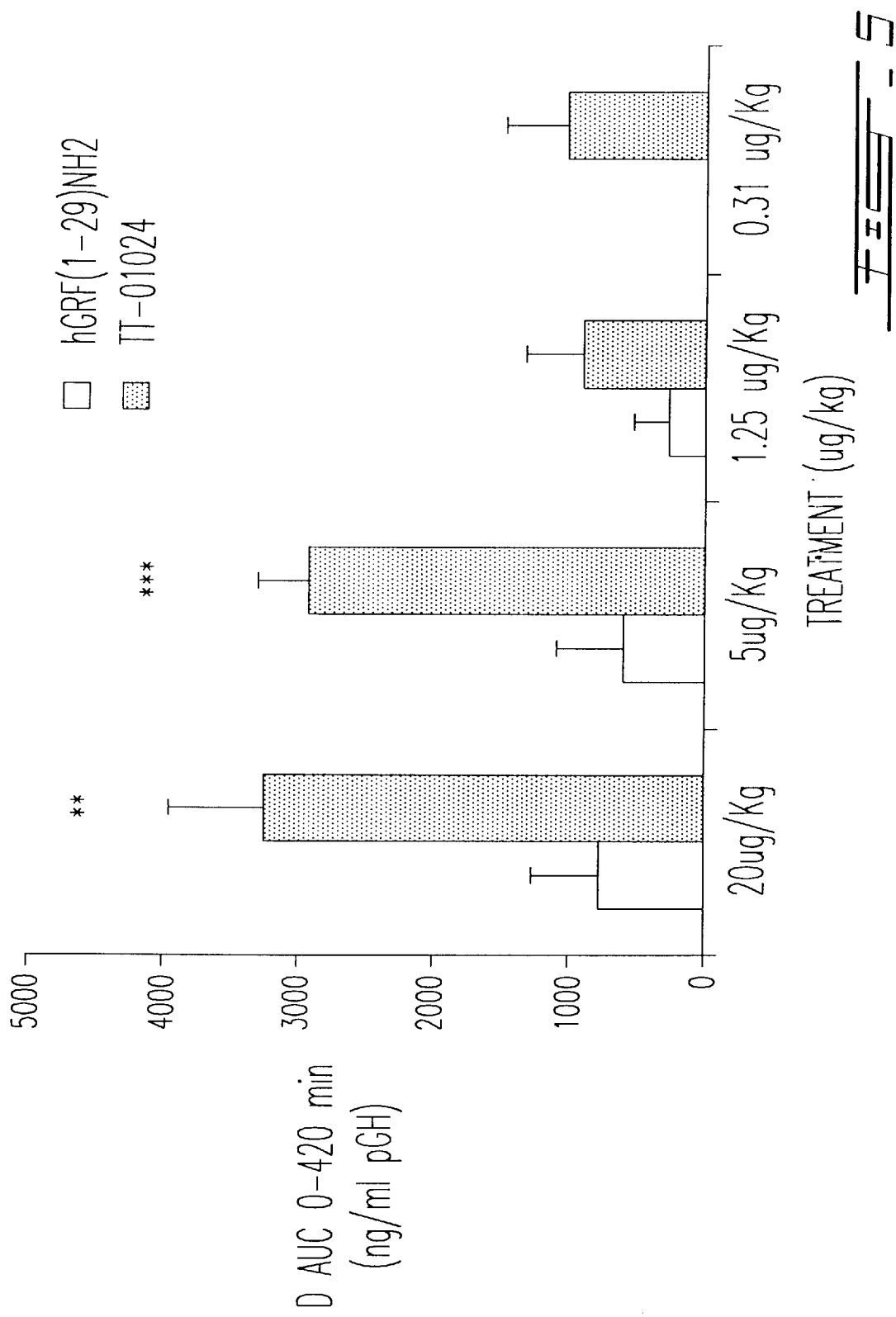

CHIMERIC FATTY BODY-PRO-GRF ANALOGS WITH INCREASED BIOLOGICAL POTENCY

RELATED APPLICATION

This application is a continuation-in-part of application Ser. No. 08/651,645 filed on May 22, 1996, now abandoned, and is a continuation-in-part of application Ser. No. 08/453,067 filed on May 26, 1995 and which is abandoned.

BACKGROUND OF THE INVENTION (a) Field of the Invention

The invention relates to chimeric fatty body-pro-GRF analogs with increased biological potency and prolonged activity, their application as anabolic agents and treatment of growth hormone deficiencies.

(b) Description of Prior Art

Growth hormone (GH) or somatotropin, secreted by the pituitary gland constitute a family of hormones which biological activity is fundamental for the linear growth of a young organism but also for the maintenance of the integrity at its adult state. GH acts directly or indirectly on the peripheral organs by stimulating the synthesis of growth factors (insulin-like growth factor-I or IGF-I) or of their receptors (epidermal growth factor or EGF). The direct action of GH is of the type referred to as anti-insulinic, which favors the lipolysis at the level of adipose tissues. Through its action on IGF-I (somatomedin C) synthesis and secretion, GH stimulate the growth of the cartilage and the bones (structural growth), the protein synthesis and the cellular proliferation in multiple peripheral organs, including muscles and the skin. Through its biological activity, GH participates within adults at the maintenance of a protein anabolism state, and plays a primary role in the tissue regeneration phenomenon after a trauma.

The decrease of GH secretion with the age, demonstrated in humans and animals, favors a metabolic shift towards catabolism which initiates or participate to the aging of an organism. The loss in muscle mass, the accumulation of adipose tissues, the bone demineralization, the loss of tissue regeneration capacity after an injury, which are observed in elderly, correlate with the decrease in the secretion of GH.

GH is thus a physiological anabolic agent absolutely necessary for the linear growth of children and which controls the protein metabolism in adults.

The secretion of GH by the pituitary gland is principally controlled by two hypothalamic peptides, somatostatin and growth hormone-releasing factor (GRF). Somatostatin inhibits its secretion, whereas GRF stimulates it.

The human GH has been produced by genetic engineering for about ten years. Until recently most of the uses of GH were concerned with growth delay in children and now the uses of GH in adults are studied. The pharmacological uses of GH and GRF may be classified in the following three major categories.

Children growth

Treatments with recombinant human growth hormone have been shown to stimulate growth in children with pituitary dwarfism, renal insufficiencies, Turner's syndrome and short stature. Recombinant human GH is presently commercialized as an "orphan drug" in Europe and in the United States for children's growth retardation caused by a GH deficiency and for children's renal insufficiencies. The other uses are under clinical trial investigation.

Long term treatment for adults and elderly patients

A decrease in GH secretion causes changes in body composition during aging. Preliminary studies of one-year treatment with recombinant human GH reported an increase in the muscle mass and in the thickness of skin, a decrease in fat mass with a slight increase in bone density in a population of aged patients. With respect to osteoporosis, recent studies suggest that recombinant human GH does not increase bone mineralization but it is suggested that it may prevent bone demineralization in post-menopausal women. Further studies are currently underway to demonstrate this theory.

Short term treatment in adults and elderly patients

In preclinical and clinical studies, growth hormone has been shown to stimulate protein anabolism and healing in cases of burn, AIDS and cancer, in wound and bone healing.

GH and GRF are also intended for veterinary pharmacological uses. Both GH and GRF stimulate growth in pigs during its fattening period by favoring the deposition of muscle tissues instead of adipose tissues and increase milk production in cows, and this without any undesired side effects which would endanger the health of the animals and without any residue in the meat or milk being produced. The bovine somatotropin (BST) is presently commercialized in the United States.

Most of the clinical studies presently undertaken were conducted with recombinant GH. The GRF is considered as a second generation product destined to replace in the near future the uses of GH in most instances. Accordingly, the use of GRF presents a number of advantages over the use of GH per se.

Physiological advantages

Growth hormone (GH) is secreted by the pituitary gland in a pulse fashion, since this rhythm of secretion is crucial for an optimal biological activity. The administration of GH to correspond to its natural mode of secretion is difficult to achieve. When GRF is administered in a continuous fashion as a slow releasing preparation or as an infusion, it increases GH secretion while respecting its pulsatility.

The recombinant GH which is presently commercialized is the 22 kDa form whereas GRF induces the synthesis and secretion from the pituitary gland of all the chemical isomers of GH which participate in a wider range of biological activities.

A treatment with GH results in a decreased capacity of the pituitary gland to secrete endogenous growth hormone, and the GH response to GRF is diminished after such a treatment. On the contrary, a treatment with GRF does not present this disadvantages, its trophic action on the pituitary gland increases this gland secreting capacity in normal animals and in patients with somatotroph insufficiency.

Economical advantages

The production of GH by genetic engineering is very expensive for clinical use. In particular, there are risks of contamination of these commercial preparation with material from the bacterial strain used. These bacterial contaminants may be pyrogens or may result in immunogenic reactions in patients. The purification of the recombinant product is effected by following a plurality of successive chromatography steps. The drastic purity criteria causes multiple quality control steps.

The synthesis of GRF is of chemical nature. The synthesis effected in a solid phase and its purification is carried out in a single step using high performance liquid chromatography (HPLC). Also the quantity of GRF to be administered is much less than the quantity of GH for the same resulting biological activity.

Even with all these advantages, GRF is still not commercialized to date as a therapeutic agent mainly because of its chemical instability. The human GRF is a peptide of 44 amino acids of the following sequence:

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
           20                  25                  30

Glu Ser Asn Gln Glu Arg Gly Ala Arg Ala Arg Leu—NH$_2$
        35                  40              (SEQ ID NO: 1).

The minimum active core is hGRF (1-29)NH$_2$

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
           20                  25          (SEQ ID NO: 2).

As for many peptides, hGRF (1–29)NH$_2$ is rapidly degraded in a serum medium and its metabolites have no residual biological activity. It has been well established that the action of enzymes, namely that of dipeptidylaminopeptidase type IV, in a blood medium results in the hydrolysis of the peptide bond Ala$^2$-Asp$^3$ of GRF. This hydrolysis results in a multitude of negative consequences which was the subject of many studies reported in the literature. Essentially, this hydrolysis leads to the formation of truncated peptides of specific activity reduced to less than 1/1000 of the biological activity.

Clinical studies with children and adults have confirmed that natural hGRF (1–44)NH$_2$ or the active fragment hGRF (1–29)NH$_2$ are not potent enough to produce equal effects corresponding to those of recombinant GH.

Many GRF analogs have been described, but they all present the disadvantages of being modified GRF having a different amino acid sequence or having synthetic amino acids (D series) added. These GRF analogs are potentially immunogenic and their administration to human may cause immunotoxicity problems and potential side effects.

It is well known that the anchoring of hydrophobic groups, such as -NEt$_2$ at the C-terminal of a peptidic sequence can result in a significantly increased specific activity. In terms of hydrophobicity, these results are contradicted by a fare number recent works such as those of Muranichi (S. Muranichi et al., 1991, Pharm. Res., 8:649–652) which stress the inefficacy of the lauroyl group as an hydrophobic group used in the synthesis of small peptides analogs. Hence, the contradictory investigations of the prior art failed to address the issue of finding a more potent GRF analog using hydrophobic residues.

Gaudreau et al. (P. Gaudreau et al., 1992, J. Med. Chem., 35(10),:1864–1869) describe the affinity of acetyl-, 6-aminohexanoyl-, and 8-aminooctanoyl-GRF(1–29)NH$_2$ with the rat pituitary receptor. In this report, none of the fatty acid-GRF compounds tested exhibited a higher affinity than hGRF(1–29)NH$_2$ itself, and the authors concluded that ". . . modifications to increase the hydrophobic character at the N-terminus of hGRF(1–29)NH$_2$ do not constitute a suitable approach to increase receptor affinity.".

Coy et al. (D. H. Cow et al., 1987, J. Med. Chem., 30:219–222) describe an acetyl-GRF peptide with an increased biological activity on a rat model, more particularly on a rat anesthetized with sodium pentobarbital. The in vitro GH response by cultured rat pituitary cells was also analyzed. However, these authors did not synthesize and test fatty acid-GRF analogs with a carbon chain longer than 2 (acetyl) added at the N-terminus region of the GRF.

Up to now, most of the GRF analogs described (including those of Gaudreau et al. and those of Coy et al.) have been tested in rat models, either in vitro or in vivo. Since human and rat GRF(1–29)NH$_2$ are markedly different, the structure-activity relationships of GRF is different in both species. Therefore, it is not possible to extrapolate results obtained in rats to human.

Accordingly, it is necessary to design GRF analogs with improved anabolic potency and having a prolonged activity. This increased potency could result from a resistance to serum degradation and/or from hyperagonistic properties.

It would be highly desirable to be provided with GRF analogs with increased anabolic potency, while remaining biodegradable and structurally closed to natural GRF, in order to prevent immune reactions when chronically injected in humans and animals.

SUMMARY OF THE INVENTION

One aim of the present invention is to provide new biodegradable and non-immunogenic pro-GRF analogs with improved biological potency and prolonged activity.

Another aim of the present invention is to provide pro-GRF analogs with increased anabolic potency and prolonged activity, i.e. capable to substantially elevate insulin-like growth factor I (IGF-I) levels when chronically administered in human and animals.

Another aim of the present invention is to provide a mean to render any pro-GRF analog more biologically potent and with a prolonged activity.

Another aim of the present invention is to provide for a method of producing active pro-GRF analogs with improved anabolic potency and prolonged activity.

The present invention relates to the preparation of chimeric fatty body-GRF analogs. These chimeric analogs include an hydrophobic moiety (tail), and can be prepared, either by anchoring one or several hydrophobic tails to the GRF, or by substituting one or several amino-acids by a pseudomicellar residue in the chemical synthesis of pro-GRF. The pro-GRF analogs in accordance with the present invention are characterized in that:

a) These analogs possess an enhanced biological activity; specifically, they are able to markedly increase GH and IGF-I blood levels when administered in an animal model closely related to human. This characteristic is particularly advantageous in that it results in a reduced dosage of an hyperactive compound being administered to the patient, thus improving treatment efficacy and reducing treatment costs.

b) Both natural amino acid and hydrophobic metabolisable substances, such as fatty acids, are used for the chemical synthesis of the pro-GRF analogs. Such a use of natural substances entirely metabolisable is intended to prevent the potential secondary effects, namely in cases of multiple administrations.

c) They present a high biological activity at infinitely small dosages.

d) They remain active for a prolonged period of time, with a high biological activity.

The use of fatty bodies in accordance with the present invention results in pro-GRF analogs which overcome all the drawbacks of the prior art. The pro-GRF analogs of the present invention are biodegradable, non-immunogenic and exhibit an improved anabolic potency with a reduced dosage and have a prolonged activity. Furthermore, the present invention deals with GRF and any of its analogs, truncated or substituted.

Unexpectedly, the results of the present invention showed that N-hexanoyl-, but not N-butyryl- or N-octanoyl-GRF (1–29)NH$_2$, statistically increased IGF-I levels when chronically administered in growing pigs. These results indicate that the addition of a C4 or a C8 chain at the N-terminus region of GRF yielded compounds with a poor biological activity when compared to the N-hexanoyl-GRF (C6-GRF). Therefore, the present invention teaches that the optimal length of the carbon chain to anchor to GRF to increase its bioactivity is C5 to C7. This result was unexpected based on the studies published by Coy et al., that demonstrated that the N-acetylation of GRF (addition of a C2 chain) increased its bioactivity in rats, and that did not document the activity of compounds with a carbon chain longer than C2.

According to the method of the present invention, these analogs can be produced either by anchoring one or several hydrophobic tails at the N- or C-terminal portion of GRF or its analogs, or by incorporating one or several pseudomicellar residues at any step of the chemical synthesis of GRF or its analogs. After cleavage and purification, the resulting modified peptide exhibits an enhanced biological activity when administered at very low dosage.

In accordance with the present invention, there is provided a chimeric fatty body-pro-GRF analog with increased biological potency, of the following general formula:

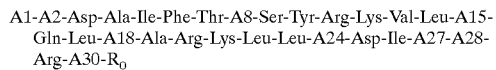

wherein,

A1 is Tyr or His;
A2 is Val or Ala;
A8 is Asn or Ser;
A15 is Ala or Gly;
A18 is Ser or Thr;
A24 is Gln or His;
A27 is Met, Ile or Nle;
A28 is Ser or Asp;
A30 is any amino acid sequence of 1 to 15 residues;
R$_0$ is NH$_2$;

wherein A1 is N- or O-anchored by a hydrophobic tail of the following general formula I:

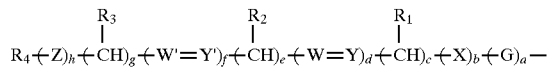

wherein,

G is a carbonyl, a phosphonyl, a sulfuryl or a sulfinyl group;
X is a oxygen atom, sulfur atom or an amino group (NH);
(W=Y) represents cis or trans (CH=CR$_5$);
(W'=Y') represents cis or trans (CH=CR$_6$);
Z is an oxygen or a sulfur atom;
R$_1$, R$_2$ and R$_3$, independently, are selected from a hydroxyl group, a hydrogen atom, and a linear or branched C$_1$–C$_6$ alkyl group;
R$_4$ is an hydroxyl group, a hydrogen atom or a linear or branched C$_5$–C$_9$ alkyl group;
R$_5$ and R$_6$, independently, are a hydrogen atom or a linear or branched C$_1$–C$_4$ alkyl group;
a is 0 or 1;
b is 0 or 1;
c is 0 to 8;
d is 0 or 1;
e is 0 to 8;
f is 0 or 1;
g is 0 to 8;
h is 0 to 1;

wherein the sum of a, b, c, d, e, f, g and h is such that the hydrophobic tail of formula I has a linear main chain of between 5 and 8 atoms (C, O and/or S).

The preferred chimeric fatty body-pro-GRF analog of the present invention is selected from the group consisting of:

a) wherein A1 is Tyr or His N-alpha anchored by hydrophobic tail of formula I, wherein both a and b=1; each of d, f and h=0; G=carbonyl; X=oxygen atom; R$_1$, R$_2$, R$_3$, R$_4$=hydrogen atom and the sum c+e+g=3, 4, 5 or 6;

b) wherein A1 is Tyr or His N-alpha anchored by hydrophobic tail of formula I, wherein a=1; each of b, d, f and h=0; G=carbonyl; R$_1$, R$_2$, R$_3$ and R$_4$=hydroxyl group and the sum c+e+g=4, 5, 6 or 7;

c) wherein A1 is Tyr or His N-alpha anchored by hydrophobic tail of formula I, wherein a=1; each of b and h=0; the sum d+f=1; G=carbonyl; R$_1$, R$_2$, R$_3$ and R$_4$=hydrogen atom and the sum c+e+g=2, 3, 4 or 5;

d) the compound of c) above wherein c is 0;

e) the compound of d) above wherein A30 is Gln-Gln-Gly-Glu-Ser-Asn-Gln-Glu-Arg-Gly-Ala-Arg-Ala-Arg-Leu;

f) the compound of e) above wherein R$_0$ is NH$_2$;

g) the compound of f) above which is cisCH$_3$—CH$_2$—CH=CH—CH$_2$—CO-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-Ala-Arg-Ala-Arg-Leu-NH$_2$ or transCH$_3$—CH$_2$—CH=CH—CH$_2$—CO-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-Ala-Arg-Ala-Arg-Leu-NH$_2$;

h) wherein A1 is Tyr or His N-alpha anchored by hydrophobic tail of formula I, wherein a=1; each of b and h=0; the sum d+f=2; G=carbonyl; R$_1$, R$_2$, R$_3$ and R$_4$=hydrogen atom and the sum c+e+g=0, 1, 2 or 3; and i) wherein A1 is Tyr or His N-alpha anchored by hydrophobic tail of formula I, wherein a=1; each of b, h, d and f=0; G=carbonyl; R$_1$, R$_2$, R$_3$ and R$_4$=hydrogen atom; and the sum c+e+g=4, 5, 6 or 7.

For the purpose of the present invention, the term "hydrophobic tail" or "Ht" is intended to mean any functionalized fatty body, such as fatty acids, fatty amines, fatty alcohols, cholesterol derivatives, etc. The term "pseudomicellar residue" or "Pr" is intended to mean any α amino acid with side chain designed so that the residue may form or adopt a micellar structure in its switterionic form.

In accordance with the present invention, there is provided a pharmaceutical formulation for inducing growth hormone release which comprises as an active ingredient a GRF analog of the present invention in association with a pharmaceutically acceptable carrier, excipient or diluent.

In accordance with the present invention, there is provided a method of increasing the level of growth hormone in a patient which comprises administering to said patient an effective amount of a GRF analog of the present invention.

In accordance with the present invention, there is provided a method for the diagnosis of growth hormone deficiencies in patients, which comprises administering to said patient a GRF analog of the present invention and measuring the growth hormone response.

In accordance with the present invention, there is provided a method for the treatment of pituitary dwarfism or growth retardation in a patient, which comprises administering to said patient an effective amount of a GRF analog of the present invention.

In accordance with the present invention, there is provided a method for the treatment of wound or bone healing in a patient, which comprises administering to said patient an effective amount of a GRF analog of the present invention.

In accordance with the present invention, there is provided a method for the treatment of osteoporosis in a patient, which comprises administering to said patient an effective amount of a GRF analog of the present invention.

In accordance with the present invention, there is provided a method for improving protein anabolism (including protein sparing effect) in human or animal, which comprises administering to said human or animal an effective amount of a GRF analog of the present invention.

In accordance with the present invention, there is provided a method for inducing a lipolytic effect in human or animal inflicted with clinical obesity, which comprises administering to said human or animal an effective amount of a GRF analog of the present invention.

In accordance with the present invention, there is provided a method for the overall upgrading of somatroph function in human or animal, which comprises administering to said human or animal an effective amount of a GRF analog of the present invention.

In the present invention the amino acids are identified by the conventional three-letter abbreviations as indicated below, which are as generally accepted in the peptide art as recommended by the IUPAC-IUB commission in biochemical nomenclature:

| Alanine | Ala |
|---|---|
| Arginine | Arg |
| Asparagine | Asn |
| Aspartic Acid | Asp |
| Cysteine | Cys |
| Glutamic Acid | Glu |
| Glycine | Gly |
| Histidine | His |
| Leucine | Leu |
| Lysine | Lys |
| Methionine | Met |
| Ornithine | Orn |
| Phenylalanine | Phe |
| Proline | Pro |
| Serine | Ser |
| Threonine | Thr |
| Tryptophane | Trp |
| Tyrosine | Tyr |
| D-Tyrosine | Tyr |
| Valine | Val |

The term "natural amino acid" means an amino acid which occurs in nature or which is incorporated as an amino acid residue in a naturally occurring peptide. In addition, the abbreviation Nle is intended to mean Norleucine.

Other abbreviations used are:

| TFA | Trifluoroacetic acid; |
|---|---|
| HOBt | 1- Hydroxybenzotriazole; |
| DIC | Diisopropylcarbodiimide; |
| DMF | Dimethylformamide; |
| Pip | Piperidine; |
| DMAP | 4-dimethylaminopyridine; |
| Boc | t-butyloxycarbonyl; |
| Fmoc | Fluorenylmethyloxycarbonyl; |
| BOP | Benzotriazo-1-yloxytris (dimethylamino) phosphonium hexafluorophosphate; |
| Me | Methyl; |
| HF | Hydrofluoric acid; |
| NEt3 | Triethylamine; and |
| TEAP | Triethylammonium phosphate (buffer). |

All the peptide sequences set out herein are written according to the generally accepted convention whereby the N-terminal amino acid is on the left and the C-terminal amino acid is on the right.

BRIEF DESCRIPTION OF THE DRAWINGS

FIG. 5 is a graph showing the effect of various doses of hGRF(1–29)$NH_2$ vs [Hexenoyl trans-3]$^0$ hGRF(1–29)$NH_2$ (TT-01024) on the GH area under the curve over 420 minutes following S.C. administration (P<0.01 and *P<0.001 when compared to the basal period—–60 to 0 min—).

DETAILED DESCRIPTION OF THE INVENTION

Figure 1:
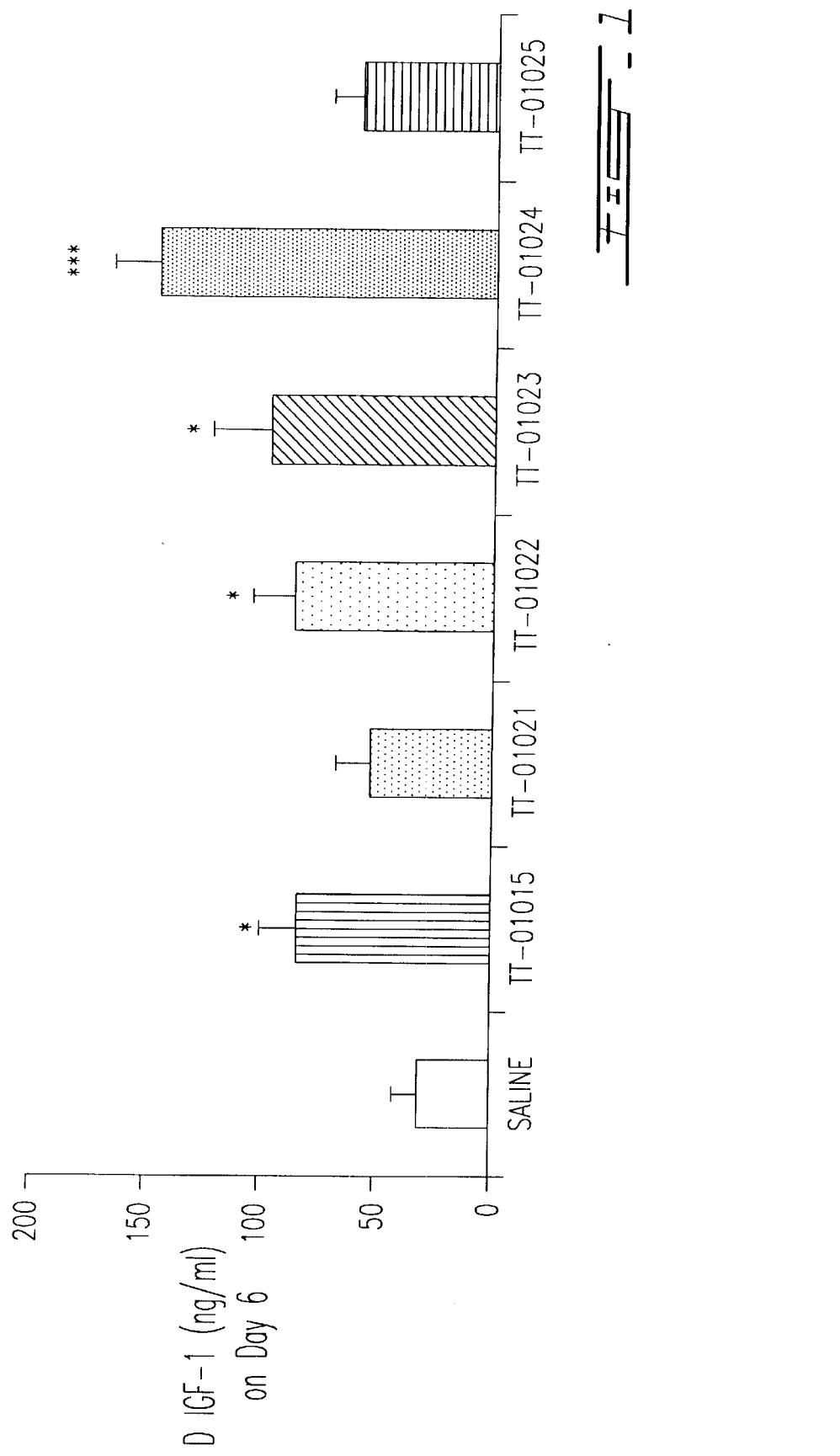
FIG. 1 is a graph of the effect of subcutaneously injected hGRF(1–29) $NH_2$ analogs on pig serum IGF-1.

The present invention relates to the use of fatty bodies, namely pseudomicellar residues and/or hydrophobic tails to produce a new family of highly potent, chimeric fatty body-pro-GRF analogs while remaining biodegradable and non immunogenic.

In accordance with the present invention, the fatty body-pro-GRF analogs can be chemically synthesized:

by anchoring one or several hydrophobic tails at the C- and/or the N-terminal portion of GRF or one of its analogs, or by incorporating one or several pseudomicellar α amino acid derivative(s) ("pseudomicellar residue") in the chemical synthesis of GRF or one of its analogs.

In accordance with the present invention, the structure of pseudomicellar residues ($P_r$) used as a link in the synthesis of GRF and analogs thereof may be represented in the following manner:

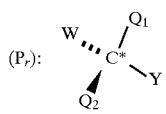

wherein:

W is a group selected from the group consisting of —CO₂Q₃; —PO₃Q₃ and —SO₃Q₃;

Q₃ is an hydrogen atom, an ammonium ion, an element selected from the group consisting the elements of group 1A of the Mendeléev periodical table, or a functional group derived from the following fatty bodies, pentenoic acids, hexenoic acids, heptenoic acids or their saturated forms;

Q₁ is a radical selected from the group consisting of alkenyl, aralkyl, aryl and alkyl ($C_{n1}H_{2n1+1}$), where $n_1$ is a number between 1 and 8. Q₁ may be selected from the following list, which is provided to illustrate the invention rather than to limit its scope:

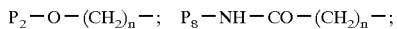

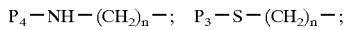

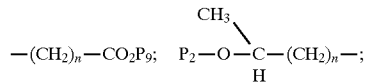

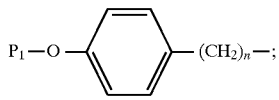

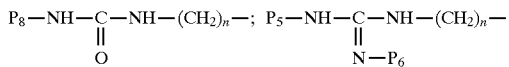

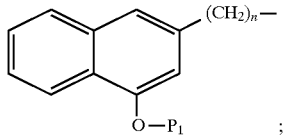

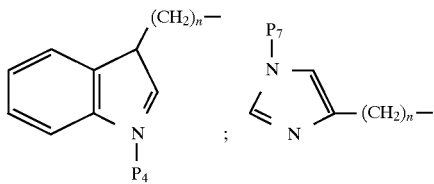

wherein,

P₁ to P₉ represents a hydrogen atom; a methyl group; a functional hydrophobic tail with a main aliphatic, alicyclic or aromatic chain, linear or branched which may be selected from the following list: saturated fatty acid of general formula ($C_mH_{2m}O_2$) with m being a value between 4 and 12; or a lateral chain protecting group as described by Gross et Meienhofer (1981, The peptides, vol. 3, Academic press: pages 1–341) such that P₁ may be a benzyl group, bromo-2 benzyl, dichloro-2,6 benzyl or t-butyl; P2 may be a benzyl group or t-butyl; P₃ may be a benzyl group, t-butyl, trityl, acetamidomethyl or benzamidomethyl; P₄ may be trifluoroacetyl, t-butyloxycarbonyl (Boc), benzyloxycarbonyl (Z) or fluorenylmethyloxycarbonyl (Fmoc); P5 may be a nitro group, p-methoxybenzenesulfonyl, mesitylenesulfonyl, or pentamethylcromane; with the proviso that P₆ is hydrogen, or that P₅ and P₆ may be adamantyloxycarbonyl; P₇ may be a phenacyl group, benzyloxymethyl or t-butoxymethyl; P₈ may be a benzhydryl group, dimetoxybenzhydryl, trityl or xanthenyl;

n is an integer between 0 and 6;

Y is of the following general formula

wherein:

A is a bivalent heteroatom, preferably oxygen, sulfur, a —NH— group or a —N(Me)— group;

$P_z$ is the same as $P_1$ to $P_4$ defined previously where Z is an integer between 1 to 4; and Q₂ is an hydrogen atom. When Q₁=H or lower alkyl, Q₂ may be any alkyl, alcoxy, alkenyl, aralkyl, or aryl group. In these conditions it possesses the same chemical identity as defined above for Q₁.

The carbon atoms on which (Q₁) and (Q₂) are attached are of L or D configuration. They are asymmetrical but not when (Q₁)=(Q₂) or (W)=(Y).

In cases where the anchoring consists in one or more hydrophobic tails (Ht) non-pseudomicellar, the whole of the structure of said tails may be represented as follows:

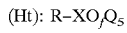

wherein:

R is an alkyl, alkenyl, aryl or aralkyl radical of branched or linear chains, and may be derived from the group of metabolisable fatty bodies consisting of saturated fatty acids of the general formula $C_mH_{2m}O_2$, preferably with m being an integer between 4 and 6; mono or polyunsaturated fatty acids, fatty amines and alcohols;

X represent a phosphorous, a carbon or a sulfur atom;

f is an integer between 1 and 3;

Q₅ represent an hydrogen atom, an ammonium ion, or an alkaline metal ion; when f is an integer between 1 and 2, Q₅ may be defined as for R above with the proviso of having at least one of the following functions:

amino (—NH—); alcohol(—OH), thio (—SH), or acid (—XO$_f$H); with X and f being as defined above.

For a better carrying out of the chemical anchoring reaction, hydrophobic tails or pseudomicellar residues functionalized under the acid form are preferably used. In these conditions, the anchoring reaction is preferably effected in a solid phase (Merrifield R. B., 1963, J. Am. Chem. Soc., 85:2149; 1964, J. Am. Chem. Soc., 86:304) using extremely active reagents such as for example Benzotriazole-1-yloxytris (dimethylamino) phosphonium hexafluorophosphate known in the prior art (B. Castro et al., 1975, Tetrahedron letters, Vol. 14:1219).

The pseudomicellar residue to be anchored is generally prepared by the direct action of a malonic salt, preferably a sodium salt of diethylacetamidomethyl malonate, and the alkyl, alkenyl, aryl or aralkyl halide in a polar solvent such as dimethylformamide. This reaction is usually followed by an acid or alkaline hydrolysis and of a resolution (preferably enzymatic) of the resulting racemic mixture.

In certain conditions, the preparation of the pseudomicellar residue consists in:

a) a first step; to protect in an orthogonal fashion and to attached on a solid support of sasrin type (M. Mergler et al., 1988, Peptides, Chemistry and Biology, Proceedings of the 10th American peptide symposium, St. Louis, p.259, G. R. Marshall, Ed., Escom, leiden), an amino acid with a functionalized lateral chain such as lysine, glutamic acid or aspartic acid; and b) a second step; to specifically deprotect the lateral chain and to anchor on the free site a metabolisable hydrophobic tail (Ht) such as described above. The pseudomicellar residue (P_r) is thus obtained after a cleavage (0.5% TFA/CH_2Cl_2) of the support-residue bond, followed by purification steps.

The pseudomicellar residue may also be prepared by a selective complexion of the acid and the amine function in alpha of a trifunctional free amino acid, by complexing agents of mineral origin such as copper acetate. In these conditions, the anchoring of the metabolisable hydrophobic tail is effected by the direct action of the formed complex and of said tail, either in its acyl halide form or in its acid or amine form in the presence of a condensation agent.

(dichloromethane), a nitrile (acetonitrile) or an amide (dimethylformamide).

With respect to the anchoring dynamic, the preferred working temperatures are between 20° and 60° C. The anchoring reaction time when hydrophobic tail used are more and more hydrophobic, varies inversely with temperature, but varies between 0.1 and 24 hours.

As an illustrative example, the triacyl lysine synthesis as set forth below illustrates in a schematic manner the whole of the anchoring principle of a hydrophobic fatty acid tail.

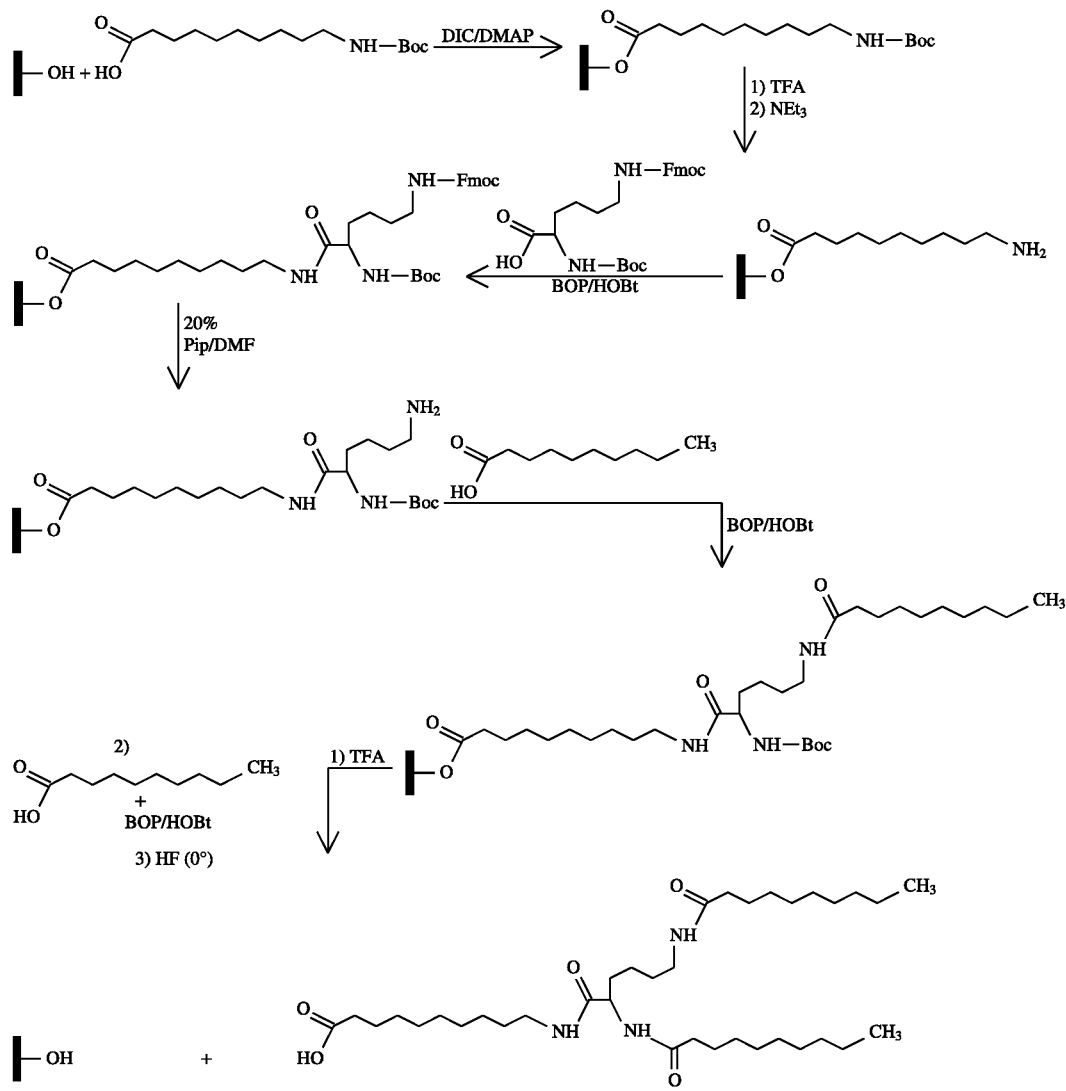

In the case where the hydrophobic tail to be anchored consists in a fatty acid, the activation in view of the anchoring may be carried out in situ. Depending on the synthesis strategies used, the peptide anchoring site is liberated just prior to the anchoring in traditional deprotection conditions (Gross et Meienhofer, 1981, The peptides, vol. 3, Academic press: pages 1–341). The hydrophobic tail (Ht) or the pseudomicellar residue (P_r) is then condensed with the anchoring agent in organic solvents such as an ether (tetrahydrofuranne), an aliphatic halogenated solvent General GRF analogs synthesis steps were carried out by solid-phase methodology on a 9050™ plus peptide synthesizer (Millipore Corporation, Milford, Mass.) using Fmoc strategy and synthesis cycles supplied by Millipore. Fmoc amino acids were supplied by Bachem California and other commercials sources. Sequential Fmoc chemistry using BOP/HOBt as coupling methodology were applied to the starting Fmoc-Pal-PEG resin (Millipore, catalog number: GEN 913383) for the production of C-terminal carboxamides. Fmoc deprotections were accomplished with piperidine 20% solution in DMF. After synthesis completion, the resin was well washed with DMF and ether prior to drying. Final cleavages of side chain protecting groups and peptide-resin bonds were performed using Millipore supplied procedure consisting of the following mixture: TFA, water, phenol, triisopropylsilane (88:5:5:2). Peptides were then precipitated and washed with ether prior to drying. Reverse phase HPLC purification (buffer A: TEAP 2.5; buffer B: 80% $CH_3CN$ in A) using a water pep 4000, absorbance 214 nm, detector model 486, flow rate 50 ml/min.; linear gradient generally from 25 to 60% B in 105 min.) followed by a desalting step (buffer C:0.1% TFA in $H_2O$; buffer D:0.1% TFA in $CH_3CH/H_2O$ 80:20) afforded peptides in yields amounting from 10 to 30% with homogeneity greater than 97% as estimated by HPLC (millennium/photodiode array detection).

In accordance with the present invention, pig was selected as a test specie, since it is a valuable preclinical model for the development of GRF analogs. Indeed, human and porcine GRF(1–29)$NH_2$ share a 100% homology of structure, and the physiological pattern of GH secretion is almost identical in both species.

Moreover, the potency of the GRF analogs was assessed as their ability to significantly increase IGF-I blood levels rather than their acute GH releasing potency. Indeed, it is known that the anabolic and healing effects of GH or GRF induced GH are mediated by an increase in IGF-I synthesis and secretion. Therefore, the measurement of GRF induced IGF-I elevation is the best indicator of the treatment efficacy.

The present invention will be more readily understood by referring to the following examples which are given to illustrate the invention rather than to limit its scope.

EXAMPLE I
EFFECT OF REPEATED ADMINISTRATIONS OF [BUTYRYL$^0$], [OCTANOYL$^0$]-, [HEXANOYL$^0$]-[HEXANOYL$^{30}$], [HEXANOYL$^{0,30}$],hGRF(1–29)$NH_2$ AND [HEXANOYL$^0$] hGRF(1–44)$NH_2$ VS HGRF(1–29) $NH_2$ ON SERUM IGF-I LEVELS IN PIGS

The objective of these experiments was to assess the potential of the GRF analogs as anabolic agents. It is known that GH or GRF-induced GH secretion exert their anabolic effect via an increase in insulin-like growth factor I (IGF-I) synthesis and secretion, that result in elevated levels of circulating IGF-I. It has been previously demonstrated that the intensity of the anabolic response to a GRF analog treatment is proportional to the increase in IGF-I levels in pigs (Dubreuil P. et al., 1990, *J. Anim. Sci.,* 68:1254–1268).

Therefore, in order to investigate the anabolic potency of the fatty acid-pro-GRF analogs, their ability to increase IGF-I levels following repeated S.C. administrations in pig was evaluated.

Experiment 1

26 Landrace×Yorkshire castrated male pigs (40–45 kg BW) were randomly distributed into 4 experimental groups:

1—hGRF(1–29)$NH_2$ (20 µg/kg, n=7)
2—[octanoyl$^0$] hGRF(1–29)$NH_2$ (20 µg/kg, n=6)
3—[hexanoyl$^0$] hGRF(1–29)$NH_2$ (20 µg/kg, n=6)
4—[butyryl$^0$] hGRF(1–29)$NH_2$ (20 µg/kg, n=7)

Each animal was injected BID (twice a day) subcutaneously for 4 consecutive days. One blood sample was collected each morning prior to the first injection of the day, and the day after the last injection, for IGF-I measurement.

Experiment 2

40 Landrace×Yorkshire castrated male pigs (40–45 kg BW) were randomly distributed into 5 experimental groups:

1—saline (n=8)
2—hGRF(1–29)$NH_2$ (40 µg/kg, n=8)
3—[hexanoyl$^0$] hGRF(1–29)$NH_2$ (10 µg/kg, n=8)
4—[hexanoyl$^0$] hGRF(1–29)$NH_2$ (20 µg/kg, n=8)
5—[hexanoyl$^0$] hGRF(1–29)$NH_2$ (40 µg/kg, n=8)

Each animal was injected BID (twice a day) subcutaneously for 5 consecutive days. One blood sample was collected each morning prior to the first injection of the day, and the day after the last injection, for IGF-I measurement.

Experiment 3:

48 Landrace×Yorkshire castrated male pigs (40–45 kg BW) were randomly distributed into 6 experimental groups:

1—Saline (n=8)
2—hGRF(1–44)$NH_2$ (30 µg/kg, n=8)
3—[hexanoyl$^0$]hGRF(1–44)$NH_2$ (30 µg/kg, n=8)
4—[hexanoyl$^0$]hGRF(1–29)$NH_2$ (20 µg/kg, n=8)
5—[hexanoyl$^0$]hGRF(1–29)$NH_2$ (20 µg/kg, n=8)
6—[hexanoyl$^{0, 30}$]hGRF(1–29)$NH_2$ (20 µg/kg, n=8)

The selected doses were 30 µg/kg for hGRF(1–44)$NH_2$ analogs and 20 µg/kg for hGRF(1–29)$NH_2$ analogs, which give identical doses on a molar basis. Each animal was injected BID (twice a day) subcutaneously for 5 consecutive days. One blood sample was collected each morning prior to the first injection of the day, and the day after the last injection, for IGF-I measurements.

IGF-I measurements

IGF-I levels were measured in pig serum by double antibody radioimmunoassay after formic acid-acetone extraction, as previously described (Abribat T. et al., 1993, J. Endocrinol., 39:583–589). The extraction prior to radioimmunoassay is a necessary step to remove endogenous IGF-binding proteins.

Statistical analysis

In both experiments, the IGF-I data were analyzed by a two way repeated measure analysis of variance, with day and treatment (GRF analog) as sources of variation. Multiple comparison procedures were there run (Student-Newman Keuls method). A P<0.05 was considered as statistically significant.

Results

Experiment 1

There were both a significant effect of day (P=0.0004) and a significant treatment×day interaction (P=0.011), indicating that the increase in IGF-I levels was dependent on the analog tested (Table 1). Blood samples for IGF-I measurements were collected daily prior to the first injection of compounds. Data are shown as mean ±SEM of 6 to 7 values per group.

TABLE 1

Effect of repeated SC injection (20μg/kg BID × 4 days)
of GRF analogs on serum IGF-I levels

| Treatment (BID, 20μg/kg SC) | Day 1 (pretreatment) (ng/ml) | Day 2 (ng/ml) | Day 3 (ng/ml) | Day 4 (ng/ml) | Day 5 (ng/ml) |
| --- | --- | --- | --- | --- | --- |
| hGRF(1–29)NH$_2$ | 252 ± 28 | 235 ± 19 | 263 ± 16 | 258 ± 17 | 262 ± 24 |
| [octanoyl$^0$]hGRF(1–29)NH$_2$ | 316 ± 22 | 287 ± 20 | 301 ± 37 | 301 ± 37 | 318 ± 39 |
| [hexanoyl$^0$]hGRF(1–29)NH$_2$ | 248 ± 20 | 281 ± 28 | 299 ± 26 | 319 ± 22[a] | 342 ± 21[a,b] |
| [butyrl$^0$]hGRF(1–29)NH$_2$ | 278 ± 20 | 281 ± 24 | 302 ± 26 | 289 ± 26 | 293 ± 23 |

Treatment P = 0.42
Day P = 0.0004
Treatment × Day P = 0.011
[a] P < 0.05 when compared to day 1
[b] P < 0.05 when compared to day 2

Multiple comparisons revealed that only [hexanoyl$^0$] hGRF(1–29)NH$_2$ elicited an increase in IGF-I levels, which was significant on days 4 (29%, P<0.05) and 5 (38%, P<0.05). Human GRF(1–29)NH$_2$ had no effect on IGF-I levels at the dose tested.

Experiment 2

There were both a significant effect of day (P<0.0001) and a significant treatment×day interaction (P<0.0001), indicating that the increase in IGF-I levels was dependent on the analog tested (Table 2). Blood samples for IGF-I measurements were collected daily prior to the first injection of the day. Data are shown as mean ±SEM of 8 values per group.

TABLE 2

| Treatment BID, SC | Day 1 (pretreatment) (ng/ml) | Day 2 (ng/ml) | Day 3 (ng/ml) | Day 4 (ng/ml) | Day 5 (ng/ml) | Day 6 (ng/ml) |
| --- | --- | --- | --- | --- | --- | --- |
| saline | 282 ± 33 | 266 ± 33 | 281 ± 34 | 293 ± 30 | 287 ± 32 | 289 ± 33 |
| hGRF(1–29)NH$_2$ (40 μg/kg) | 244 ± 24 | 243 ± 16 | 267 ± 20 | 275 ± 27 | 267 ± 17 | 256 ± 15 |
| [hexanoyl$^0$]hGRF (1–29)NH$_2$ (10μg/kg) | 303 ± 31 | 327 ± 20 | 337 ± 25 | 338 ± 25 | 366 ± 37[a] | 350 ± 34[a] |
| [hexanoyl$^0$]hGRF (1–29)NH$_2$ (20 μg/kg) | 302 ± 38 | 341 ± 37 | 368 ± 43[a] | 362 ± 40[a] | 362 ± 45[a] | 368 ± 57[a] |
| [hexanoyl$^0$]hGRF (1–29)NH$_2$ (40 μg/kg) | 252 ± 35 | 275 ± 32 | 319 ± 31[a] | 354 ± 41[a,b] | 350 ± 34[a,b] | 374 ± 33[a,b,c] |

Treatment P = 0.23; Day P = 0.0001
Treatment × Day P = 0.0001
[a] P < 0.05 when compared to day 1
[b] P < 0.05 when compared to day 2
[c] P < 0.05 when compared to day 3

Multiple comparisons revealed that all three tested doses of [hexanoyl$^0$] hGRF(1–29)NH$_2$ increased IGF-I levels. At 10 μg/kg, IGF-I levels were significantly increased at days 5 and 6 (16 to 21%, P<0.05). At 20 μg/kg, they were increased at days 3, 4, 5 and 6 (20 to 22%, P<0.05). At 40 μg/kg, they were increased at days 3, 4, 5 and 6 (27 to 48%, P<0.05). The serum IGF-I levels remained stable in saline— and hGRF(1–29)NH$_2$—treated pigs.

Finally, a regression analysis revealed that the increase in IGF-I concentrations from day 1 to day 6 was dependent on the dose of [hexanoyl$^0$] hGRF(1–29)NH$_2$ (ΔIGF-I=11.9+ (2.77 * dose); r=0.68, P<0.0001).

Experiment 3:

There were both a significant effect of day (P<0.0001) and a significant treatment×day interaction (P<0.0001), indicating that the increase in IGF-I levels was dependent on the analog tested (Table IV). Multiple comparison revealed that analogs with an hexanoyl function branched at the N-terminal region of GRF were highly potent:

[hexanoyl$^0$] hGRF(1–29)NH$_2$ significantly increased IGF-I levels on days 5 and 6 (by 28% and 31%, P<0.05)

[hexanoyl$^{0, 30}$] hGRF(1–29)NH$_2$ significantly increased IGF-I levels on days 4, 5 and 6 (by 32%, 35% and 43%, P<0.05)

[hexanoyl$^0$] hGRF(1–44)NH$_2$ significantly increased IGF-I levels on days 3, 4, 5 and 6 (by 41%, 54%, 50% and 61%, P<0.05)

As previously observed for hGRF(1–29)NH$_2$ (experiments 1 and 2), the full length hGRF(1–44)NH$_2$ had little or no effect on IGF-I levels (except for a significant effect on day 5, which was not sustained on day 6). Finally, the anchoring of an hexanoyl function at the C-terminal region of hGRF(1–29)NH$_2$ yielded an analog with increased potency when compared to hGRF(1–29)NH$_2$ (21% increased in IGF-I levels on day 6, P<0.05), but less potent than [hexanoyl$^0$]hGRF(1–29)NH$_2$.

Human GRF(1–29)NH$_2$ and hGRF(1–44)NH$_2$ were injected at 20 μg/kg and 30 μg/kg, respectively, in order to achieve equimolar concentrations. Data shown are mean ±SEM of 8 values per group.

TABLE 3

Effect of multiple SC injections of GRF analogs (BID × 5 days) on serum IGF-I levels in growing pigs

| Treatment BID, SC | Day 1 (pretreatment) (ng/ml) | Day 2 (ng/ml) | Day 3 (ng/ml) | Day 4 (ng/ml) | Day 5 (ng/ml) | Day 6 (ng/ml) |
|---|---|---|---|---|---|---|
| saline | 215 ± 21 | 215 ± 28 | 219 ± 25 | 226 ± 28 | 249 ± 30 | 234 ± 24 |
| hGRF(1–44)NH$_2$ (30µg/kg) | 245 ± 21 | 254 ± 22 | 285 ± 26 | 297 ± 28 | 303 ± 26[a] | 296 ± 26 |
| [hexanoyl$^0$]hGRF(1–29)NH$_2$ (20µg/kg) | 272 ± 45 | 292 ± 52 | 292 ± 57 | 315 ± 57 | 347 ± 44[a,b,c] | 356 ± 44[a,b,c] |
| [hexanoyl$^{30}$]hGRF(1–29)NH$_2$ (20µg/kg) | 297 ± 30 | 270 ± 25 | 287 ± 24 | 278 ± 18 | 276 ± 20 | 327 ± 24[b] |
| [hexanoyl$^{0,30}$]hGRF(1–29)NH$_2$ (20µg/kg) | 205 ± 24 | 212 ± 26 | 253 ± 33 | 271 ± 36[a,b] | 277 ± 29[a,b] | 294 ± 26[a,b] |
| [hexanoyl$^0$]hGRF(1–44)NH$_2$ (30µg/kg) | 241 ± 30 | 290 ± 33 | 340 ± 41[a] | 372 ± 40[a,b] | 361 ± 46[a,b] | 388 ± 49[a,b,c] |

Treatment P = 0.16
Day P < 0.0001
Treatment × Day P < 0.0001
[a]P < 0.05 when compared to day 1
[b]P < 0.05 when compared to day 2
[c]P < 0.05 when compared to day 3

Conclusions

Neither hGRF(1–29)NH$_2$ nor hGRF(1–44)NH$_2$ at doses ranging from 20 to 40 µg/kg were able to modulate IGF-I levels. However, the anchoring of fatty acid rendered GRF more potent and yielded analogs with markedly improved activity on IGF-I secretion. The anchoring of fatty acids was efficient in improving the anabolic potency of both hGRF (1–29)NH$_2$ and hGRF(1–44)NH$_2$. From the above results, it is concluded that the ideal fatty acid to use is hexanoic acid or any C$_6$ fatty derivative, and that it should be preferably anchored at the N-terminal region of GRF to yield maximally potent analogs.

EXAMPLE II

Comparative effects of pro-GRF analogs on IGF-I levels in pigs

This was a 5-day treatment, twice a day S.C. administration of one single dose of each test article vs saline. This experiment was conducted to compare the efficacy of (Aminohexanoyl)$_0$ hGRF (1–29) NH$_2$, (Hexylformiate)$_0$ hGRF (1–29) NH$_2$, (Hexenoyl trans-2)$_0$ hGRF (1–29) NH$_2$, (Hexenoyl trans-3)$_0$ hGRF (1–29) NH$_2$ and (Muconoyl)$_0$ hGRF (1–29) NH$_2$ to that of (Hexanoyl)$_0$ hGRF (1–29) NH$_2$.

All tested compounds belong to the same family of GRF analogs: they are a combination of the natural GRF and natural fatty acids, designed to improve the activity of the molecule.

Identity of tested analogs:

| | | in saline |
|---|---|---|
| TT-01015 | (Hexanoyl)$_0$ hGRF (1–29) NH$_2$ | 20 µg/kg |
| TT-01021 | (Aminohexanoyl)$_0$ hGRF (1–29) NH$_2$ | 20 µg/kg |
| TT-01022 | (Hexylformiate)$_0$ hGRF (1–29) NH$_2$ | 20 µg/kg |
| TT-01023 | (Hexenoyl trans-2)$_0$ hGRF (1–29) NH$_2$ | 20 µg/kg |
| TT-01024 | (Hexenoyl trans-3)$_0$ hGRF (1–29) NH$_2$ | 20 µg/kg |
| TT-01025 | (Muconoyl)$_0$ hGRF (1–29) NH$_2$ | 20 µg/kg |

Route and frequency of test article
ADMINISTRATION: Two daily subcutaneous injections.
TEST SYSTEM: Landrace×Yorkshire pigs.
ANIMAL DESCRIPTION: Fifty six (56) growing barrows pigs weighing 35 kg at the time of purchase.
RATION: Commercial feed concentrate (18% protein) offered ad libitum.
EXPERIMENTAL DESIGN: Fifty six (56) pigs were randomly distributed into 7 experimental groups (n=8 pigs per group). Each group received two daily S.C. administration of the following treatments (volume: 3 ml, S.C. injection).
group 1: saline 2×/day
group 2: TT-01015 20 µg/kg 2×/day
group 3: TT-01021 20 µg/kg 2×/day
group 4: TT-01022 20 µg/kg 2×/day
group 5: TT-01023 20 µg/kg 2×/day
group 6: TT-01024 20 µg/kg 2×/day
group 7: TT-01025 20 µg/kg 2×/day Treatments were administered from day 1 to 5. Immediately before the injections, one blood sample were collected from each animal, and additional blood samples were collected on day 6.

Blood samples were allowed to clot, serum was harvested by centrifugation and submitted to IGF-I assays.

Results are shown in FIG. 1 as D-IGF-I, which is defined as the increase in IGF-I levels from day 1 (pretreatment levels) to day 6 (after 5 days of GRFs administrations). Among all analog tested, only hexanoyl-, hexylformiate-, hexenoyl trans2- and hexenoyl trans3-hGRF(1–29)NH$_2$ significantly increased IGF-I levels over the 6-day study period, whereas aminohexanoyl and muconoyl-hGRF(1–29)NH$_2$ did not. Since hGRF(1–29)NH$_2$ has been shown to be ineffective at the same dose in the same conditions in previous assays (see Example I), these results show that the addition of various C6 carbon chains at the N-terminus region of GRF increases its bioactivity.

EXAMPLE III

Intravenous GH-releasing potency of (Hexenoyl trans-3)$_0$ hGRF (1–29) NH$_2$ vs hGRF(1–29)NH$_2$ in pigs This experiment was conducted to test the I.V. acute GH-releasing potency of (Hexenoyl trans-3)$_0$ hGRF (1–29) NH$_2$, a pro-GRF analog, in a model physiologically close to human and to compare it to that of hGRF(1–29)NH$_2$.

(Hexenoyl trans-3)$_0$ hGRF (1–29) NH$_2$ is a combination of the natural hGRF(1–29)NH$_2$ and natural fatty acids. This study was a multidose, single I.V. injection study.

Identity of tested analogs:

| | | |
|---|---|---|
| TT-01024 | (Hexenoyl trans-3)$_0$ hGRF (1–29) NH$_2$ | 0.25 µg/kg |
| TT-01024 | (Hexenoyl trans-3)$_0$ hGRF (1–29) NH$_2$ | 1 µg/kg |
| TT-01024 | (Hexenoyl trans-3)$_0$ hGRF (1–29) NH$_2$ | 4 µg/kg |
| hGRF(1–29)NH$_2$ | | 0.25 µg/kg |
| hGRF(1–29)NH$_2$ | | 1 µg/kg |
| hGRF(1–29)NH$_2$ | | 4 µg/kg |

Route and frequency of test article
ADMINISTRATION: intravenous acute injection.
TEST SYSTEM: Landrace×Yorkshire pigs.
ANIMAL DESCRIPTION: Fifty six (56) growing barrows pigs weighing 35 kg at the time of purchase.
RATION: Commercial feed concentrate (18% protein) offered ad libitum.
EXPERIMENTAL DESIGN: Fifty (56) pigs (4 spare animals) were cannulated (a catheter surgically implanted in one jugular vein) within on week, before the study. On days 1 and 7, cannulated animals were randomly distributed into 7 groups (n=4 pigs per group).

| | |
|---|---|
| group 1: saline | |
| group 2: TT-01024 | 0.25 µg/kg |
| group 3: TT-01024 | 1 µg/kg |
| group 4: TT-01024 | 4 µg/kg |
| group 5: hGRF(1–29)NH$_2$ | 0.25 µg/kg |
| group 6: hGRF(1–29)NH$_2$ | 1 µg/kg |
| group 7: hGRF(1–29)NH$_2$ | 4 µg/kg |

Blood samples for pGH assay were collected every 20 min from 1 hour before to 5 hours after GRF injections, with additional samplings 10 and 30 min after injection (n=21 samples). Blood samples are allowed to clot at +4° C. Serum will be harvested by centrifugation, stored at −20° C. and submitted to pGH assays.

Figure 2:
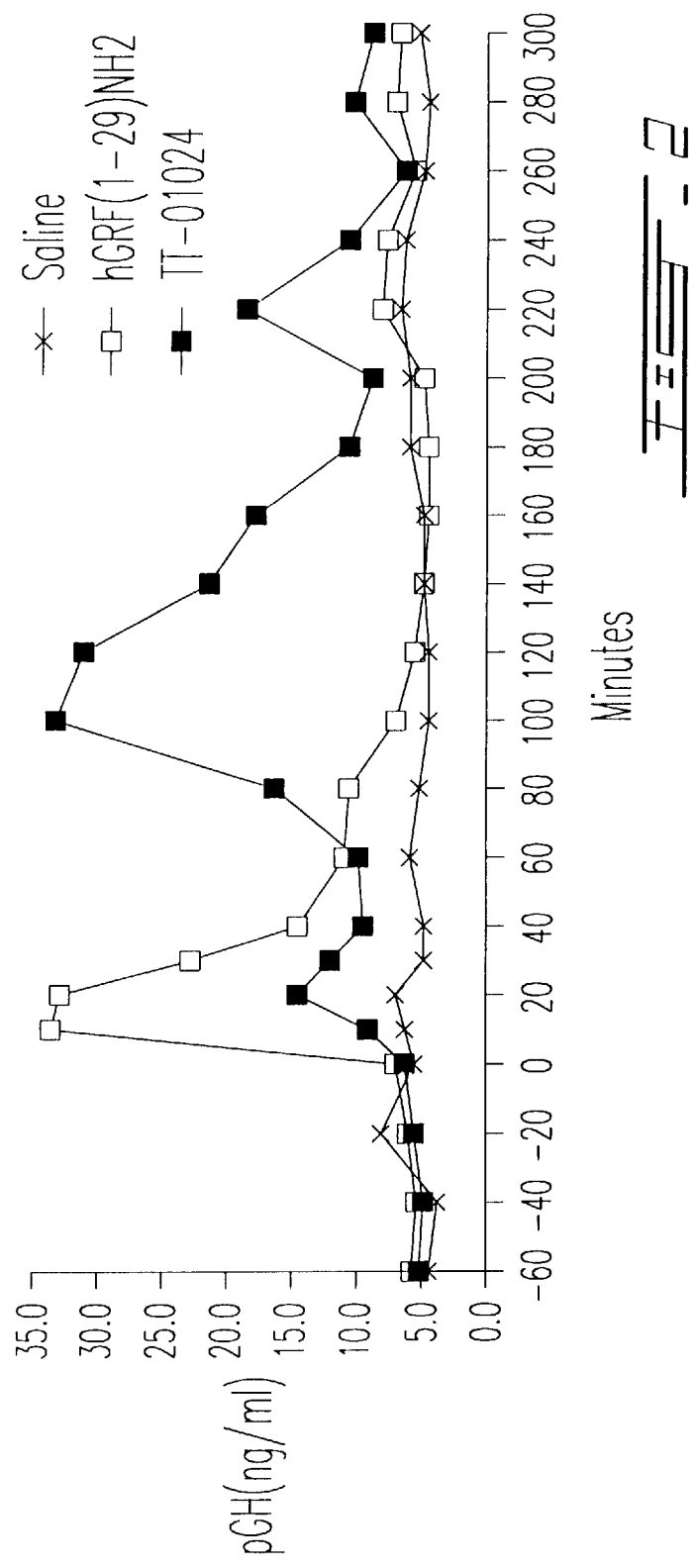
FIG. 2 is a curve of the effect of one intravenous injection of (4 µg/kg) hGRF(1–29) $NH_2$ and (4 µg/kg) (Hexenoyl trans-3)$_0$ hGRF (1–29) $NH_2$ (TT-01024)+analog on pig serum GH.
Figure 3:
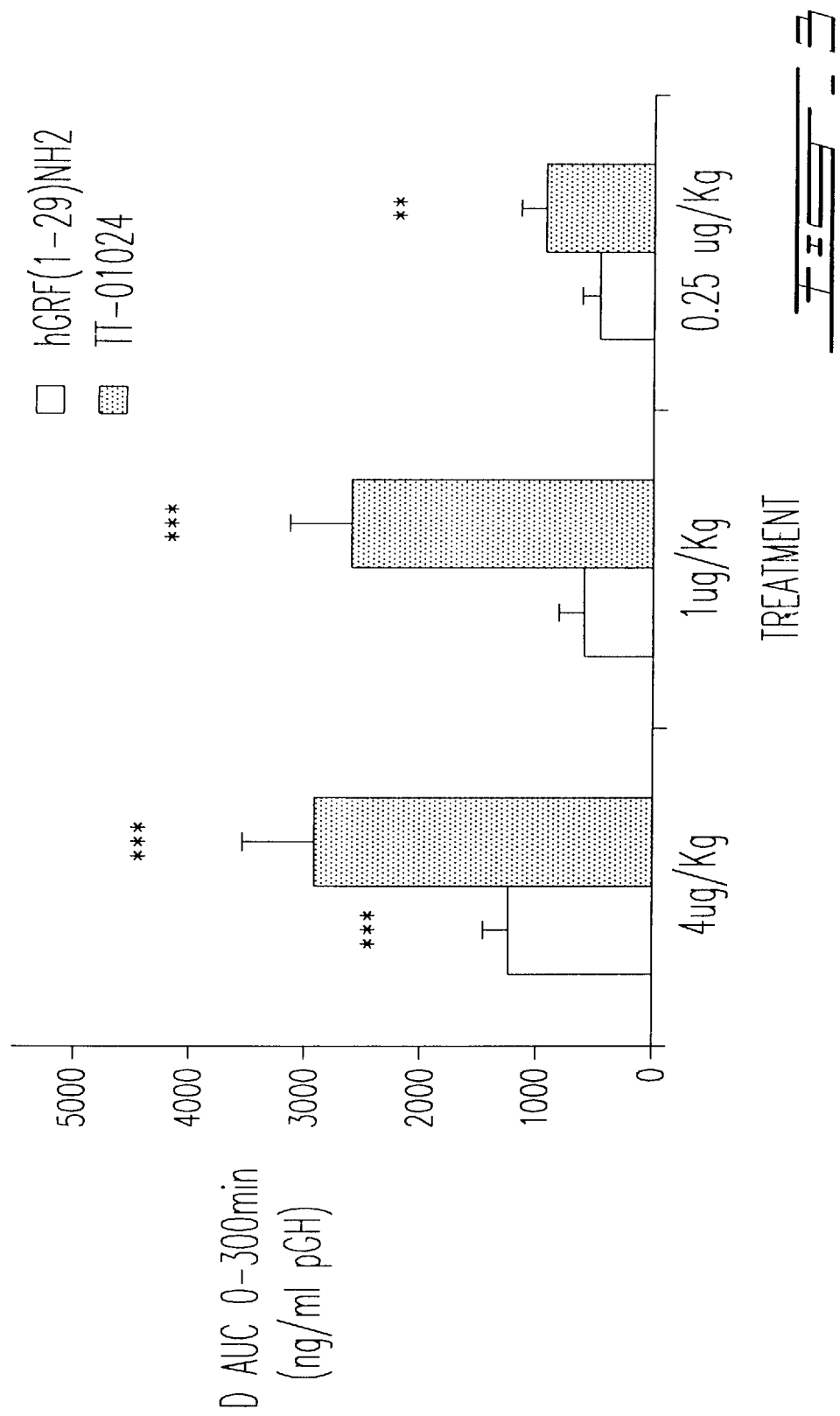
FIG. 3 is a graph showing the effect of various doses of hGRF(1–29)$NH_2$ vs [hexenoyl trans-3]$^0$ hGRF(1–29)$NH_2$ (TT-01024) on the GH area under the curve over 300 minutes following I.V. administration (P<0.01 and *P<0.001 when compared to the basal period—–60 to 0 min—)

Results are illustrated in FIGS. 2 and 3. As shown in FIG. 2, hGRF(1–29)NH$_2$ (4 µg/kg) induced a rapid GH release that was sustained for approximately 60 minutes following injection. In contrast, hexenoyl trans3-hGRF(1–29)NH$_2$ injected at the same dose increased GH levels over a longer period, approximately 260 minutes. In addition, the GH response in the first 60 minutes was moderate, suggesting that this analog acts as a pro-GRF, being processed in serum into native GRF in the minutes or hours following injection. As shown in FIG. 3, which presents the effects of various doses of GRF and the analog on the GH area under the curve (0 to 300 minutes following injection), hGRF(1–29)NH$_2$ produced a significant effect on GH secretion at 4 µg/kg, but not at 0.25 or 1 µg/kg, whereas hexenoyl trans3-hGRF (1–29)NH$_2$ elicited a significant response at all 3 doses tested. In conclusion, these results show that hexenoyl trans3-hGRF(1–29)NH$_2$ is a GRF analog with increased potency on GH secretion, and suggest that it may act as a pro-GRF, being protected from enzymatic degradation in serum.

EXAMPLE IV

Subcutaneous GH-releasing potency of (Hexenoyl trans-3)$_0$ hGRF (1–29) NH$_2$ vs hGRF(1–29)NH$_2$ in pigs This experiment was conducted to test the S.C. acute GH-releasing potency of (Hexenoyl trans-3)$_0$ hGRF (1–29) NH$_2$, a pro-GRF analog, in a model physiologically close to human and to compare it to that of hGRF(1–29)NH$_2$.

Identity of tested analogs:

| | | |
|---|---|---|
| TT-01024 | (Hexenoyl trans-3)$_0$ hGRF (1–29) NH$_2$ | 0.31 µg/kg |
| TT-01024 | (Hexenoyl trans-3)$_0$ hGRF (1–29) NH$_2$ | 1.25 µg/kg |
| TT-01024 | (Hexenoyl trans-3)$_0$ hGRF (1–29) NH$_2$ | 5 µg/kg |
| TT-01024 | (Hexenoyl trans-3)$_0$ hGRF (1–29) NH$_2$ | 20 µg/kg |
| hGRF(1–29)NH$_2$ | | 1.25 µg/kg |
| hGRF(1–29)NH$_2$ | | 5 µg/kg |
| hGRF(1–29)NH$_2$ | | 20 µg/kg |

Route and frequency of test article
ADMINISTRATION: Subcutaneous acute injection.
TEST SYSTEM: Landrace×Yorkshire pigs.
ANIMAL DESCRIPTION: Sixty four (64) growing barrows pigs weighing 35 kg at the time of purchase.
RATION: Commercial feed concentrate (18% protein) offered ad libitum.
EXPERIMENTAL DESIGN: Thirty six (36) pigs (4 spare animals) were cannulated (a catheter surgically implanted in one jugular vein) within one week, before the study. On days 1 and 7, cannulated animals were randomly distributed into 8 groups (n=4 pigs per group).

| | |
|---|---|
| group 1: saline | |
| group 2: TT-01024 | 0.31 µg/kg |
| group 3: TT-01024 | 1.25 µg/kg |
| group 4: TT-01024 | 5 µg/kg |
| group 5: TT-01024 | 20 µg/kg |
| group 6: hGRF(1–29)NH$_2$ | 1.25 µg/kg |
| group 7: hGRF(1–29)NH$_2$ | 5 µg/kg |
| group 8: hGRF(1–29)NH$_2$ | 20 µg/kg |

Blood samples for pGH assay were collected every 20 min from 1 hour before to 7 hours after GRF injections, (n=25 samples). Blood samples were allowed to clot at +4 CC. Serum is harvested by centrifugation, stored at −20° C. and submitted to pGH assays.

Figure 4:
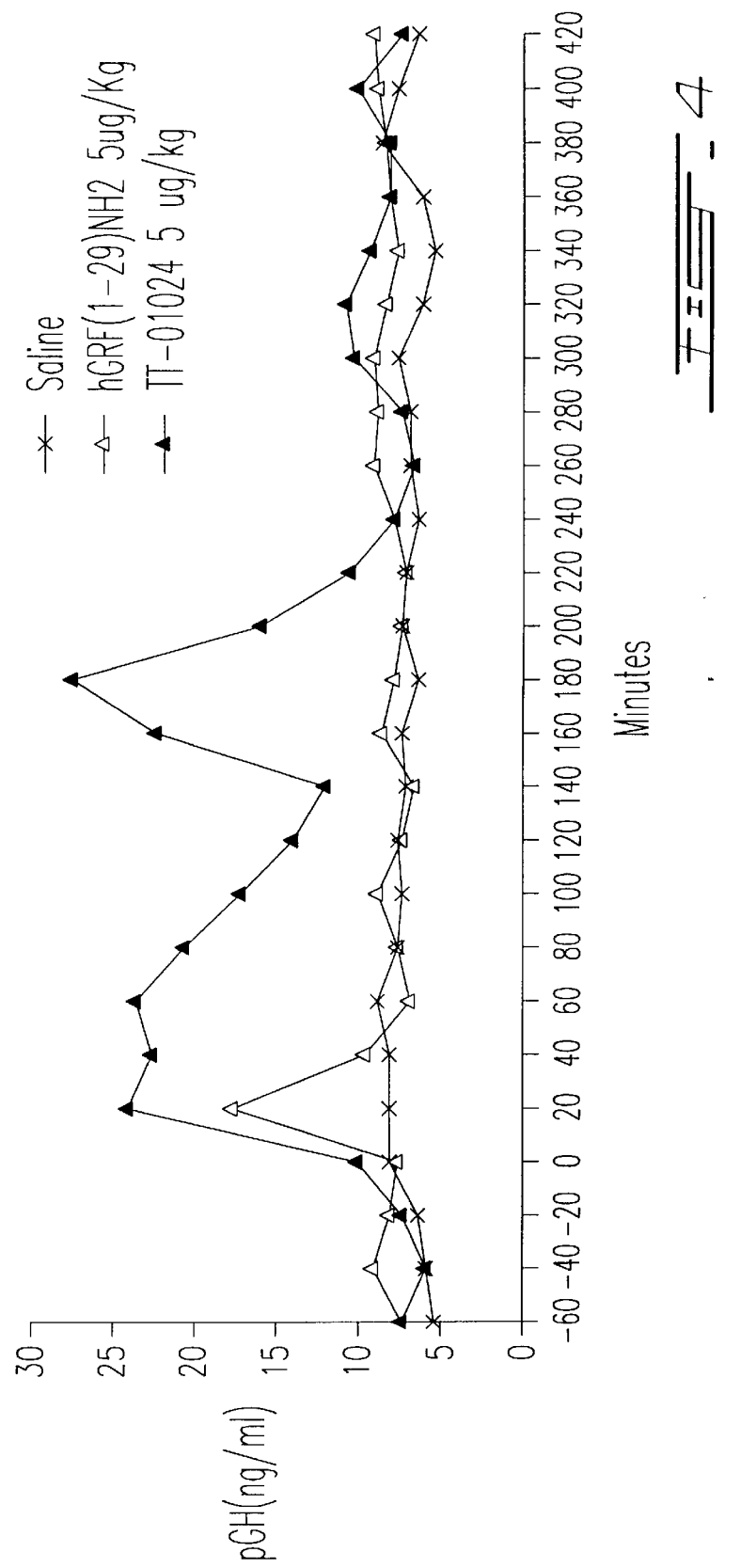
FIG. 4 is a curve of the effect of one subcutaneous injection of 5 µg/kg hGRF(1–29) $NH_2$ and (5 µg/kg) (Hexenoyl trans-3)$_0$ hGRF (1–29) $NH_2$ analog on pig serum GH.

Results are shown in FIGS. 4 and 5. As shown in FIG. 4, the subcutaneous injection of 5 µg/kg hGRF(1–29)NH$_2$ induced a GH response in the first 60 minutes following administration, whereas the same injection of hexenoyl trans3-hGRF(1–29)NH$_2$ induced a GH response that was sustained for 240 minutes. The FIG. 5 illustrates the effect of various doses of the GRFs tested on the GH area under the curve over the study period, i.e. from 0 to 420 minutes following injection. Over this period, hGRF(1–29)NH$_2$ did not induce any significant GH response at any of the tested doses, whereas hexenoyl trans3-hGRF(1–29)NH$_2$ elicited significant increases of the GH AUC at 5 and 20 µg/kg. Altogether, these results suggest that hexenoyl trans3-hGRF (1–29)NH$_2$ is a highly potent GH secretagogue, even when subcutaneously administered.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A chimeric fatty bodyGRF analog with increased biological potency, of the following general formula:

A1-A2-Asp-Ala-Ile-Phe-Thr-A8-Ser-Tyr-Arg-Lys-Val-Leu-A15-Gln-Leu-A18-Ala-Arg-Lys-Leu-Leu-A24-Asp-Ile-A27-A28-Arg-A30-R$_0$ wherein, A1 is Tyr or His;
A2 is Val or Ala;
A8 is Asn or Ser;
A18 is Ser or Thr;
A15 is Ala or Gly;
A24 is Gln or His;
A27 is Met, Ile or Nle;
A28 is Ser or Asp;
A30 is any amino acid sequence of 1 to 15 residues;
R$_0$ is NH2;

wherein A1 is N-anchored by a hydrophobic tail of the following general formula I:

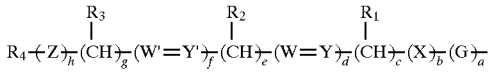

wherein,

G is a carbonyl group;
X is a oxygen atom, sulfur atom or an amino group (NH);
(W=Y) represents cis or trans (CH=CR5);
(W'=Y') represents cis or trans (CH=CR6);
Z is an oxygen or a sulfur atom;
R$_1$, R$_2$ and R$_3$, independently, are selected from a hydrogen atom, and a linear or branched C$_1$–C$_6$ alkyl group;
R$_4$ is a hydrogen atom;
R$_5$ and R$^6$, independently, are a hydrogen atom or a linear or branched C$_1$–C$_4$ alkyl group;
a is 1;
b is 0;
c is 0 to 3;
d is 0 or 1;
e is 0 to 3;

f is 0 or 1;

g is 0 to 4;

h is 0 to 1;

wherein the sum of d+f=1 or 2 and the sum of a, b, c, d, e, f, g and h is such that the hydrophobic tail of formula I has a linear main chain of between 5 and 7 carbon atoms.

2. The chimeric fatty bodyGRF analog of claim 1, wherein c is 0.

3. The chimeric fatty bodyGRF analog of claim 2, wherein A30 is Gln-Gln-Gly-Glu-Ser-Asn-Gln-Glu-Arg-Gly-Ala-Arg-Ala-Arg-Leu.

4. The chimeric fatty bodyGRF analog of claim 3, wherein $R_0$ is $NH_2$.

5. The chimeric fatty bodyGRF analog of claim 4, of the formula cisCH$_3$—CH$_2$—CH=CH—CH$_2$—CO-Tyr-Ala-Asp-Ala-Ile-Phe-Thr-Rsn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-Ala-Arg-Ala-Arg-Leu-NH$_2$ or transCH$_3$—CH$_2$—CH=CH—CH$_2$—CO-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu-Ser-AsH-Gln-Glu-Arg-Gly-Ala-Arg-Ala-Arg-Leu-NH$_2$.

6. The chimeric fatty bodyGRF analog of claim 1, wherein the sum d+f=2; $R_1$, $R_2$, $R_3$ and $R_4$=hydrogen atom and the sum c+e+g=2, 3 or 4.

7. The chimeric fatty bodyGRF analog of claim 1, wherein $R_1$, $R_2$, $R_3$ and $R_4$=hydrogen atom; and the sum c+e+g=3, 4 or 5.

8. The chimeric fatty body GRF analog of claim 4, of the formula transCH$_3$—CH$_2$—CH=CH—CH$_2$—CO-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-Ala-Arg-Ala-Arg-Leu-NH$_2$.

9. A pharmaceutical formulation for inducing growth hormone release which comprises as an active ingredient a GRF analog as claimed in claims 1 or 8, in association with a pharmaceutically acceptable carrier, excipient or diluent.

10. A method of increasing the level of growth hormone in a patient which comprises administering to said patient an effective amount of a GRF analog as claimed in claims 1 or 8.

11. A method for the diagnosis of growth hormone deficiencies in patients, which comprises administering to said patient a GRF analog as claimed in claims 1 or 8 and measuring the growth hormone response.

12. A method for the treatment of pituitary dwarfism or growth retardation in a patient, which comprises administering to said patient an effective amount of a GRF analog as claimed in claims 1 or 8.

13. A method for the treatment of wound or bone healing in a patient, which comprises administering to said patient an effective amount of a GRF analog as claimed in claims 1 or 8.

14. A method for the treatment of osteoporosis in a patient, which comprises administering to said patient an effective amount of a GRF analog as claimed in claims 1 or 8.

15. A method for improving protein anabolism in human or animal, which comprises administering to said human or animal an effective amount of a GRF analog as claimed in claims 1 or 8.

16. A method for inducing a lipolytic effect in human or animal inflicted with clinical obesity, which comprises administering to said human or animal an effective amount of a GRF analog as claimed in claims 1 or 8.

17. A method for the overall upgrading of somatroph function in human or animal, which comprises administering to said human or animal an effective amount of a GRF analog as claimed in claims 1 or 8.

* * * * *

UNITED STATES PATENT AND TRADEMARK OFFICE
CERTIFICATE OF CORRECTION

PATENT NO. : 5,861,379
APPLICATION NO. : 08/702114
DATED : January 19, 1999
INVENTOR(S) : Michel Ibea, Thierry Abribat and Paul Brazeau It is certified that error appears in the above-identified patent and that said Letters Patent is hereby corrected as shown below:

Claim 1, col. 21, line 59: delete "Thr" and substitute "Thr;"

Claim 1, col. 21, line 65: delete "NH2" and substitute "$NH_2$"

Claim 1, col. 22, line 54: delete "CR5" and substitute "$CR_5$"

Claim 1, col. 22, line 55: delete "CR6" and substitute "$CR_6$"

Claim 1, col. 22, line 60: delete "$R^6$" and substitute "$R_6$"

Claim 5, line 16: delete "Rsn" and substitute "Asn"

Claim 5, line 22: delete "AsH" and substitute "Asn"

Signed and Sealed this

Sixth Day of July, 2010

David J. Kappos
*Director of the United States Patent and Trademark Office*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 44 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( x i ) SEQUENCE DESCRIPTION: SEQ ID NO:1:

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
         35                  40

( 2 ) INFORMATION FOR SEQ ID NO:2:

( i ) SEQUENCE CHARACTERISTICS:
( A ) LENGTH: 29 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( x i ) SEQUENCE DESCRIPTION: SEQ ID NO:2:

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25